(12) United States Patent
Cinader, Jr. et al.

(10) Patent No.: US 11,642,199 B2
(45) Date of Patent: May 9, 2023

(54) DENTAL APPLIANCE WITH COSMETIC THERAPEUTIC AQUEOUS SOLUTION

(71) Applicant: 3M Innovative Properties Company, St. Paul, MN (US)

(72) Inventors: David K. Cinader, Jr., Woodbury, MN (US); Joel D. Oxman, Minneapolis, MN (US); Yizhong Wang, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 1013 days.

(21) Appl. No.: 16/140,376

(22) Filed: Sep. 24, 2018

(65) Prior Publication Data
US 2020/0093576 A1 Mar. 26, 2020

(51) Int. Cl.
*A61C 7/08* (2006.01)
*A61C 7/00* (2006.01)
*A61Q 11/00* (2006.01)
*B33Y 80/00* (2015.01)
*A61K 6/76* (2020.01)
*A61C 19/06* (2006.01)
*A61C 7/36* (2006.01)

(52) U.S. Cl.
CPC .............. *A61C 7/08* (2013.01); *A61C 7/002* (2013.01); *A61C 7/36* (2013.01); *A61C 19/063* (2013.01); *A61K 6/76* (2020.01); *A61Q 11/00* (2013.01); *B33Y 80/00* (2014.12)

(58) Field of Classification Search
CPC .. A61C 7/08; A61C 7/002; A61C 7/36; A61C 19/063; B33Y 80/00; A61K 6/76; A61K 8/24; A61Q 11/00; A61Q 11/02
See application file for complete search history.

(56) References Cited

U.S. PATENT DOCUMENTS

| | | | | |
|---|---|---|---|---|
| 3,935,305 A | * | 1/1976 | Delaney | A61K 8/19 424/49 |
| 4,097,588 A | * | 6/1978 | Levine | A61K 8/21 424/52 |
| 4,585,649 A | * | 4/1986 | Lynch | A61Q 11/00 424/48 |
| 5,783,217 A | * | 7/1998 | Lee | A61L 27/12 424/602 |
| 5,993,785 A | * | 11/1999 | Johansen | A61P 31/22 424/49 |

(Continued)

FOREIGN PATENT DOCUMENTS

| CN | 101938979 A | 1/2011 |
|---|---|---|
| WO | WO 2001-30305 | 5/2001 |

(Continued)

*Primary Examiner* — Edward Moran
*Assistant Examiner* — Matthew P Saunders

(57) ABSTRACT

A system includes a dental appliance having a polymeric shell with a plurality of cavities for receiving one or more teeth; and a biocompatible cosmetic aqueous liquid in the cavities of the polymeric shell of the dental appliance. The aqueous liquid includes a viscosity modifier chosen from a water compatible polymer, a polysaccharide, a silica compound, and mixtures and combinations thereof, a tooth re-mineralizing agent, and water. The aqueous liquid is substantially free of tooth whitening agents and fluoride, and has a refractive index of greater than 1.3 at room temperature.

65 Claims, 3 Drawing Sheets

(56) References Cited

U.S. PATENT DOCUMENTS

| | | | | |
|---|---|---|---|---|
| 6,054,119 | A * | 4/2000 | Hurme | A23G 4/064 |
| | | | | 424/435 |
| 6,183,248 | B1 | 2/2001 | Chishti | |
| 6,387,981 | B1 | 5/2002 | Zhang | |
| 6,572,693 | B1 | 6/2003 | Wu | |
| 7,905,724 | B2 | 3/2011 | Kuo | |
| 8,445,558 | B2 * | 5/2013 | Karim | A61K 6/871 |
| | | | | 523/116 |
| 9,468,652 | B2 | 10/2016 | Zuk | |
| 9,795,543 | B1 * | 10/2017 | Jiao | A61Q 11/00 |
| 9,849,310 | B2 | 12/2017 | Kutsch | |
| 10,406,078 | B2 * | 9/2019 | Jiao | A61K 6/74 |
| 2006/0078688 | A1 * | 4/2006 | DeSimone | C08F 2/46 |
| | | | | 427/496 |
| 2006/0115782 | A1 | 6/2006 | Li | |
| 2006/0115785 | A1 | 6/2006 | Li | |
| 2009/0305196 | A1 * | 12/2009 | Karim | A61C 5/70 |
| | | | | 433/222.1 |
| 2012/0129135 | A1 | 5/2012 | Yang et al. | |
| 2012/0301408 | A1 * | 11/2012 | Baker | A61K 8/736 |
| | | | | 424/49 |
| 2017/0100214 | A1 * | 4/2017 | Wen | G16H 30/20 |
| 2018/0140511 | A1 * | 5/2018 | Jiao | A61C 7/08 |
| 2019/0060523 | A1 * | 2/2019 | Bakry | C03C 3/19 |
| 2021/0177549 | A1 * | 6/2021 | Connell | B08B 1/002 |

FOREIGN PATENT DOCUMENTS

| | | |
|---|---|---|
| WO | WO 2001-30306 | 5/2001 |
| WO | WO 2001-30307 | 5/2001 |
| WO | WO 2003-063804 | 8/2003 |

* cited by examiner

DENTAL APPLIANCE WITH COSMETIC THERAPEUTIC AQUEOUS SOLUTION

BACKGROUND

Orthodontic treatments reposition misaligned teeth and improve bite configurations for improved cosmetic appearance and dental function. The teeth are repositioned by applying controlled forces to the teeth over an extended time period.

Teeth may be repositioned by placing a polymeric incremental position adjustment appliance, generally referred to as an orthodontic aligner or an orthodontic aligner tray, over the teeth of the patient for each treatment stage of an orthodontic treatment. The orthodontic alignment trays include a polymeric shell with a plurality of cavities for receiving one or more teeth. The individual cavities in the polymeric shell are shaped to exert force on one or more teeth to resiliently and incrementally reposition selected teeth or groups of teeth in the upper or lower jaw. A series of orthodontic aligner trays are provided for wear by a patient sequentially and alternatingly during each stage of the orthodontic treatment to gradually reposition teeth from one tooth arrangement to a successive tooth arrangement to achieve a desired tooth alignment condition. Once the desired alignment condition is achieved, an aligner tray, or a series of aligner trays, may be used periodically or continuously in the mouth of the patient to maintain tooth alignment.

In addition, orthodontic retainer trays may be used for an extended time period to maintain tooth alignment following the initial orthodontic treatment. Mouthguards and nightguards may also be used to temporarily protect teeth during athletic activities or to prevent damage caused by tooth-to-tooth contact or rubbing.

An orthodontic treatment or use of a retainer or a protective mouthguard may require that an orthodontic appliance remain in the mouth of the patient for up to 22 hours a day, over an extended time period of days, weeks, months, or even years.

Saliva is the mouth's primary defense against tooth decay. Healthy saliva flow helps prevent cavities by physically removing bacteria from the oral cavity before they can become attached to tooth and tissue surfaces and form a protected biofilm. The flow of saliva also helps dilute sugars and acids introduced by intake of food and beverages. The buffering capacity of saliva neutralizes acids and aids in the digestive process.

SUMMARY

Placement of a dental appliance such as, for example, an orthodontic aligner tray, a retainer tray, a mouthguard, a nightguard, and the like, over the teeth of a patient can impede the natural flow of saliva around the teeth, which in some cases may increase the risk of tooth decay, particularly if the patient fails to consistently follow recommended regimens for tray cleaning and tooth brushing.

In addition, the nature of the action of orthodontic appliances dictates that the individual cavities in the polymeric shell be intentionally designed to fit imperfectly around select teeth of the patient, as this misfit causes the orthodontic aligner trays to deflect and exert correctional forces to those select teeth targeted for realignment. This misfit creates an air gap between the orthodontic appliance and some of the teeth of the patient. Even if the orthodontic appliance is made from a transparent polymeric material, air, liquids consumed by the patient, saliva, and entrained bubbles in the liquids, all residing in the air gap can cause the aligner tray to be more readily visible in the mouth of the patient, which creates a non-ideal aesthetic appearance. An orthodontic appliance that is substantially invisible over the teeth during treatment is most desirable for the patient.

In general, the present disclosure is directed to a system including a dental appliance, such as an orthodontic aligner tray, an orthodontic retainer tray, a mouthguard, a nightguard, and the like, that includes a polymeric shell with tooth-retaining cavities. At least some of the tooth-retaining cavities contain a biocompatible cosmetic therapeutic aqueous liquid. In some embodiments, the aqueous liquid has a chemical composition selected to maintain or improve the oral health of the patient such as, for example, a tooth re-mineralizing agent, a buffering agent, and mixtures and combinations thereof. In some embodiments, the aqueous liquid at least partially occupies the air gap between the orthodontic aligner tray and the teeth, as has a chemical composition with a refractive index selected to render the orthodontic aligner tray less visible in the mouth of the patient. In some embodiments, the aqueous liquid can provide at least one of a tooth re-mineralizing, buffering, and an aesthetic benefit for the patient.

In one aspect, the present disclosure is directed to a system including a dental appliance having a polymeric shell with a plurality of cavities for receiving one or more teeth; and a biocompatible cosmetic aqueous liquid in the cavities of the polymeric shell of the dental appliance. The aqueous liquid includes a viscosity modifier chosen from a water compatible polymer, a polysaccharide, a silica compound, and mixtures and combinations thereof, a tooth re-mineralizing agent, and water. The aqueous liquid is substantially free of tooth whitening agents and fluoride, and has a refractive index of greater than 1.3 at room temperature.

In another aspect, the present disclosure is directed to a system including a dental appliance having a polymeric shell with a plurality of cavities for receiving one or more teeth, wherein the polymeric shell is a polymeric material chosen from polyethylene terephthalate, polyethylene terephthalate glycol, poly cyclohexylenedimethylene terephthalate glycol, and mixtures and combinations thereof; and a biocompatible cosmetic aqueous liquid in at least some of the cavities of the polymeric shell of the dental appliance. The aqueous liquid includes about 0.1 parts by weight to about 60 parts by weight of a viscosity modifier chosen from polysaccharides, water compatible polymers, silica compounds, and mixtures and combinations thereof; about 40 parts by weight to about 95 parts by weight of a buffering agent including a phosphate compound; up to about 1 part by weight of a tooth re-mineralizing agent including a calcium compound; and water. The aqueous liquid is substantially free of tooth whitening agents and fluoride.

In another aspect, the present disclosure is directed to a method in which a tooth is inserted in a cavity in a polymeric shell of a dental appliance to adjust the tooth from a maloccluded position to a desired position. The method includes applying in the cavity a biocompatible cosmetic aqueous liquid comprising a viscosity modifier chosen from polysaccharides, water compatible polymers, silica compounds and mixtures and combinations thereof; a tooth re-mineralizing agent; and water. The aqueous liquid is substantially free of tooth whitening agents and fluoride and has a refractive index greater than 1.3.

In another aspect, the present disclosure is directed to a kit including a dental appliance having a polymeric shell with a plurality of cavities for receiving one or more teeth; and a biocompatible cosmetic aqueous liquid. The cosmetic aqueous liquid includes a viscosity modifier chosen from polysaccharides, water compatible polymers, silica compounds, and mixtures and combinations thereof; a tooth re-mineralizing agent; and water. The aqueous liquid is substantially free of tooth whitening agents and fluoride, and has a refractive index of greater than 1.3.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the drawings indicate like elements.

DETAILED DESCRIPTION

Figure 1:
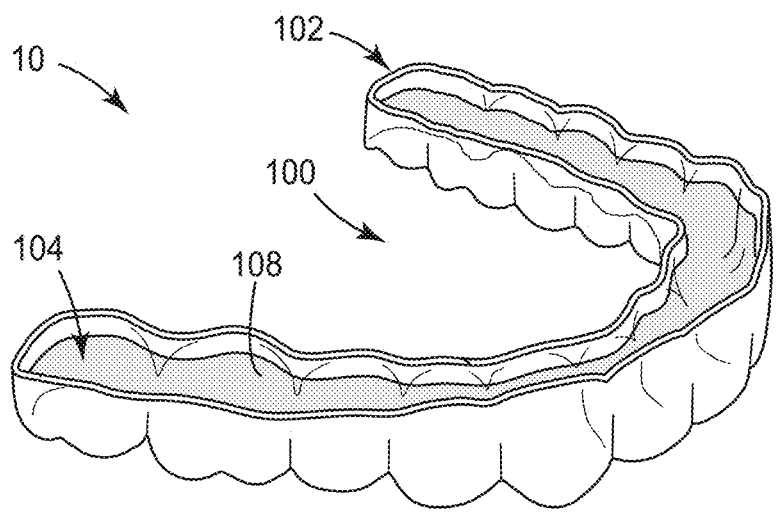
FIG. 1 is a schematic overhead perspective view of a system including a dental appliance and a cosmetic aqueous solution.

In one embodiment, a system 10 includes a dental appliance 100 as shown in FIG. 1, which includes a thin polymeric shell 102 with tooth-retaining cavities 104 configured to fit over one or more of the teeth in the upper or lower jaw of a patient. In the embodiment shown in FIG. 1, the dental appliance 100 is an orthodontic aligner tray, but in other embodiments the dental appliance can be, for example, an orthodontic retainer tray, a mouthguard, or a nightguard. In the embodiment of FIG. 1, the tooth-retaining cavities 104 are shaped to receive and resiliently reposition one or more teeth from one tooth arrangement to a successive tooth arrangement. In other embodiments, a dental retainer tray may include tooth-retaining cavities 104 shaped to receive and maintain the position of the previously realigned one or more teeth, while a mouthguard or a nightguard includes tooth-retaining cavities 104 shaped to protect teeth during sports activities or to prevent teeth in the upper and lower jaws from rubbing against one another and causing premature wear to a tooth surface.

The system 10 includes the dental appliance 100 with at least some of the tooth-retaining cavities 104 of the polymeric shell 102 containing a biocompatible cosmetic aqueous liquid 108. The term cosmetic herein refers to compositions such as those described in the Federal Food, Drug and Cosmetic Act, sec. 201(i). In this application the term cosmetic means that the aqueous liquid is not intended for use as a drug to cure or treat a disease in the mouth of the patient, but includes components intended to be used in the polymeric shell 102 and in the mouth of a patient for cleansing, beautifying, or promoting attractiveness of the teeth, altering the appearance of the teeth, or reducing the visibility of the polymeric shell 102 when placed over the teeth. In various embodiments, the term biocompatible means that the aqueous liquid includes components suitable for use in the mouth of a patient, and is not toxic, injurious, or physiologically reactive with the bodily fluids in the mouth or with the exposed surfaces of the teeth, and will not adversely react with commonly consumed foods and drinks.

Disclosed aqueous liquid compositions 108, one or more components in the compositions, or both, can be characterized as edible. Referring to a component or composition as edible means that the particular ingredient or composition is safe for daily, long-term ingestion at recommended use levels. In some embodiments, the GRAS (generally regarded as safe) list from the United States Food and Drug Administration (FDA) can be utilized to determine if a component is edible at the levels utilized in a composition.

The aqueous liquid 108 in the alignment system 10 includes a viscosity modifier chosen from a water compatible polymer, a polysaccharide, a silica compound, and mixtures and combinations thereof; a tooth re-mineralizing agent; and water, and is biocompatible. The aqueous liquid is at least substantially free of tooth whitening agents and fluoride.

In the present application, substantially free of tooth whitening agents and fluoride means that the aqueous liquid 108 includes no more than about 1 wt % of either tooth whitening agents or fluoride, based on the total weight of the aqueous liquid. Non-limiting examples of suitable fluorides include inorganic fluoride sources such as sodium fluoride, sodium monofluoride, stannous fluoride, calcium fluoride and the like, as well as organic fluoride sources such as tetraalkylammonium tetrafluoroborate salts and amine hydrofluoric acid salts, and mixtures and combinations thereof. Examples of tooth whitening agents, which again are not intended to be limiting, include hydrogen peroxide, carbamide peroxide, calcium peroxide, and mixtures and combinations thereof. In some embodiments, the aqueous liquid is essentially free of tooth whitening agents and fluoride, which means that the aqueous liquid includes no more than about 0.1 wt % of tooth whitening agents or fluoride. In some embodiments, the aqueous liquid is completely free of tooth whitening agents and fluoride, which means that the aqueous liquid includes no more than about 0.01 wt % of tooth whitening agents or fluoride.

In some embodiments, the aqueous liquid 108 in the system 10 has a refractive index selected to minimize the refractive index difference between the polymeric shell of the dental appliance and the air gap between the teeth of a patient and the dental appliance occupied by the aqueous liquid. This matching of refractive index enhances the optical properties of the system 10 by reducing glare and reflectance at the surface of the teeth of the patient. Glare is defined herein as the average reflectance over a range of 450-650 nanometers and reflectance is defined herein as the process where a fraction of the radiant flux incident on a surface is returned into the same hemisphere whose base is the surface and which contains the incident radiation (see Handbook of Optics, $2^{nd}$ ed., McGraw-Hill, Inc, 1995).

In some embodiments, the refractive index of the aqueous liquid 108 is selected to minimize both the appearance of air bubbles entrained in the aqueous liquid, and the appearance of the dental appliance 100 overlying the teeth of the patient. The selection of the refractive index of the aqueous liquid 108 depends at least in part on the refractive index of the polymeric material of the polymeric shell 102. In various example embodiments, which are not intended to be limiting, the polymeric shell 102 is a polymeric material having refractive indexes (RI) in the range of 1.48 to 1.65. For example, polymethyl(meth)acrylate (PMMA) has a RI of 1.489; polycarbonate has a RI of 1.585; and polyethylene terephthalate (PET) has a RI of 1.64. In some non-limiting embodiments, which are provided only as example, if the polymeric shell is PET having a RI of about 1.6, to minimize the appearance of the dental appliance over the teeth of the patient, the refractive index of an aqueous liquid free of visible bubbles should be greater than about 1.3, or greater than about 1.33, or greater than about 1.34 (+0.01) at a room temperature of about 20° C. to about 25° C. The refractive index of the aqueous liquid 108 can be measured by, for example, a refractometer such as those available from Bausch & Lomb, Rochester, N.Y.

In some embodiments, the aqueous liquid 108 optionally includes nanoparticles selected to modify the refractive indices of components of the composition, and provide the aqueous liquid 108 with desired aesthetic properties. By utilizing a filler of nanoparticles, such as a metal oxide nanofiller, dispersed in the aqueous solution 108, the refractive index can be increased, which can provide a much more optically transparent or translucent material, or a more closely index matched material.

Suitable nanoparticle fillers may include, but are not limited to, silica; zirconia; oxides of titanium, aluminum, cerium, tin, yttrium, strontium, barium, lanthanum, zinc, ytterbium, bismuth, iron, and antimony; and combinations thereof. More typical nanofillers may include zirconia ($ZrO_2$), oxides of titanium (e.g., $TiO_2$), and ytterbium (e.g, $Y_2O_3$), and other metal oxides with high refractive indices. Titanium dioxide and zirconia are particularly useful nanofillers, as they have very high refractive indices, and will require less weight of material than a lower refractive index material to match the refractive indices appropriately.

The nanofillers typically have an average particle size of at most 100 nanometers and more typically at most 50 nanometers. Such nanofillers typically have an average particle size of at least 2 nanometers, more typically at least 5 nanometers, and even more typically at least 10 nanometers. In some embodiments, the nanofiller is in the form of nanoclusters, typically at least 80 percent by weight nanoclusters. In other embodiments, the nanofiller is in the form of a combination of nanoparticles and nanoclusters. Often a portion of the surface of the nanofiller is silane treated or otherwise chemically treated to provide one or more desired physical properties. Suitable nanofillers are disclosed in U.S. Pat. No. 6,387,981 (Zhang et al.) and U.S. Pat. No. 6,572,693 (Wu et al.) as well as International Publication Nos WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof.

In some embodiments, the aqueous liquid 108 of the system 10 is substantially colorless and transparent to visible light with a wavelength of 400-750 nm, and as such when free of visible bubbles appears to be substantially invisible against the teeth of the patient. In some embodiments, the polymeric shell 102 and the aqueous liquid 108 of the system 10 transmit at least 60%, or at least 80%, or at least 90%, of incident light with a wavelength of about 400-750 nm, which can render the system 10 substantially invisible when the polymeric shell 102 is positioned over the teeth of the patient.

To provide a desired viscosity for a particular application, the aqueous liquid 108 in the system 10 includes a viscosity modifier chosen from a water compatible polymer, a polysaccharide, a silica compound, and mixtures and combinations thereof. In various embodiments, the viscosity modifier may be bacteriostatic and possesses low odor. Alternatively, bacteriostatic or odor removing agents can be added to the aqueous liquid.

Water compatible polymers suitable as viscosity modifiers in the aqueous liquid 108 include water soluble polymers, water dispersible polymers, and mixtures and combinations thereof.

Water soluble polymers dissolve, disperse, or swell in water and thus modify the physical properties of the aqueous liquid 108 to provide properties such as, for example, gellation, thickening, or emulsification/stabilization. Suitable biocompatible, water soluble polymers include, but are not limited to, polyacrylic acid and salts thereof, polyethylene glycol, ethylene oxide/propylene oxide copolymers, and mixtures and combinations thereof, as well as polymeric materials such as dextran, hydroxypropyl cellulose, and polystyrene sulfonic acid and salts thereof.

When combined with additional compounds such as, for example, anionic or nonionic surfactants, acids or bases, water compatible polymers dissolve, disperse, or swell in water and thus modify the physical properties of the aqueous liquid 108 to provide properties such as, for example, gellation, thickening, or emulsification/stabilization. Suitable water compatible polymers include, but are not limited to, synthetic polymers, modified natural polymers and natural polymers such as, for example, chitosan, neutralized chitosan, modified chitosan, partially deacetyl chitin, acrylate polymers with amine side group such as those available under the trade designation EUDRAGIT brand of polymers, specifically EUDRAGIT E PO Ready Mix, available from Evonik Nutrition & Care GmbH, and mixtures and combinations thereof.

In some embodiments, the aqueous liquid 108 includes one or more surfactants. In some embodiments, useful surfactants can include those of Formula I:

$$HOCH_2-(CHOH)_n-CH_2NR^1R^2 \quad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; and n is an integer from about 2 to about 5.

In Formula I, the groups $R^1$ and $R^2$ are independently selected from the group consisting of a hydrogen atom, an alkyl group, $C(O)R^3$, and $SO_2R^4$. Each of $R^1$ and $R^2$ may be a hydrogen atom, each of $R^1$ and $R^2$ may be an alkyl group, each of $R^1$ and $R^2$ may be $C(O)R^3$, or each of $R^1$ and $R^2$ may be $SO_2R^4$. In some embodiments, $R^1$ may be a hydrogen atom and $R^2$ may be an alkyl group, $C(O)R^3$, or $SO_2R^4$. In other embodiments, $R^1$ may be an alkyl group, and $R^2$ may be $C(O)R^3$, or $SO_2R^4$. In still other embodiments, $R^1$ may be $C(O)R^3$, and $R^2$ may be $SO_2R^4$. When either or both of $R^1$ and $R^2$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group includes less than about thirty carbon atoms, less than about twenty-six carbon atoms, or less than about twenty carbon atoms. In some embodiments, the alkyl group includes a straight chain alkyl group. In other embodiments, the alkyl group includes a branched alkyl group. In still other embodiments, the alkyl group includes a cyclic alkyl group. When each of $R^1$ and $R^2$ includes an alkyl group, $R^1$ and $R^2$ may comprise the same alkyl group, or $R^1$ and $R^2$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopentyl, and cyclooctyl.

The groups $R^3$ and $R^4$ are independently selected from the group consisting of an alkyl group, an aryl group, and an aralkyl group. When either or both of $R^3$ or $R^4$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group includes less than about thirty carbon atoms, less than about twenty-six carbon atoms, or less than about twenty carbon atoms. In some embodiments, the alkyl group includes a straight chain alkyl group. In other embodiments, the alkyl group includes a branched alkyl group. In still other embodiments, the alkyl group includes a cyclic alkyl group. In compounds of Formula I or pharmaceutically acceptable salts thereof, when both $R^3$ and $R^4$ groups are present, and when each of $R^3$ and $R^4$ includes an alkyl group, $R^3$ and $R^4$ may comprise the same alkyl group, or $R^3$ and $R^4$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopentyl, and cyclooctyl.

When either or both of $R^3$ or $R^4$ are an aryl group, the aryl group may comprise one arene ring or more than one arene ring. Arene rings may include up to six carbon atoms, up to eight carbon atoms, up to ten carbon atoms, up to twelve carbon atoms, up to fourteen carbon atoms, up to sixteen carbon atoms, or up to eighteen carbon atoms. Arene rings may comprise a heteroatom, for example, nitrogen, oxygen, or sulfur. If more than one arene ring is present, the arene rings may be fused together, or they may be joined by a chemical bond. In compounds of Formula I or pharmaceutically acceptable salts thereof, when both $R^3$ and $R^4$ groups are present, and when each of $R^3$ and $R^4$ includes an aryl group, $R^3$ and $R^4$ may comprise the same aryl group, or $R^3$ and $R^4$ may comprise different aryl groups. Non-limiting examples of aryl groups include substituted and unsubstituted phenyl, 1-naphthyl, 2-naphthyl, 9-anthracenyl.

When either or both of $R^3$ or $R^4$ are an aralkyl group, the aralkyl group may comprise one arene ring or more than one arene ring. The aralkyl group may comprise up to six carbon atoms, up to eight carbon atoms, up to ten carbon atoms, up to twelve carbon atoms, up to fourteen carbon atoms, up to sixteen carbon atoms, up to eighteen carbon atoms, or up to twenty carbon atoms. If more than one arene ring is present in the aralkyl group, the arene rings may be fused together, or they may be joined by a chemical bond. Arene rings may comprise a heteroatom, for example, nitrogen, oxygen, or sulfur. In compounds of Formula I or pharmaceutically acceptable salts thereof, when both $R^3$ and $R^4$ groups are present, and when each of $R^3$ and $R^4$ includes an aralkyl group, $R^3$ and $R^4$ may comprise the same aralkyl group, or $R^3$ and $R^4$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In Formula I, n is an integer from about 2 to about 5. In some embodiments, the dental composition includes a compound of Formula I, or a pharmaceutically acceptable salt thereof, wherein n is an integer having a value of about 5, about 4, about 3, or about 2. In some embodiments, n is an integer having a value of 5, or 4, or 3, or 2. It is understood that the dental composition may comprise more than one compound of Formula I, or a pharmaceutically acceptable salt thereof, and that the compounds may be represented by Formula I with different integer values of n. In these embodiments, the average value of n of a composition may be a non-integer.

Pharmaceutically acceptable salts of compounds of Formula I can also be utilized and can include ammonium salts. In some embodiments, the dental composition of the invention includes an ammonium salt. An ammonium salt may be represented as the reaction product of an acid with an amine, or as the reaction product of an amine with an alkylating agent such as, for example, iodomethane, bromoethane, or benzyl bromide. An ammonium salt includes a protonated amine compound, for example a compound of Formula I in which a $NR^1R^2$ group, wherein $R^1$ and $R^2$ are independently selected from the group consisting of a hydrogen atom and an alkyl group, has been protonated with an inorganic acid or an organic acid. An ammonium salt includes an alkylated amine compound, for example a compound of Formula I in which a $NR^1R^2$ group, wherein $R^1$ and $R^2$ are independently selected from the group consisting of a hydrogen atom and an alkyl group, has been alkylated with an alkylating agent.

An ammonium salt includes at least one counter ion that may be an inorganic anion, an organic anion, or a combination of anions. A combination of anions includes a combination of more than one inorganic anion, a combination of more than one organic anion, or a combination of an inorganic ion and an organic anion. Inorganic ions include, for example, halide (fluoride, chloride, bromide, and iodide), nitrate, sulfate, tetrafluoroborate, and tetra(aryl)borates. Tetra(aryl)borates include compounds having the formula $Z_4B^-$, where Z is an aromatic group, for example a substituted or unsubstituted phenyl group. Examples of tetra(aryl)borates include, but are not limited to, tetraphenylborate, tetrakis(4-methylphenyl)borate, tetrakis(2-methylphenyl)borate, tetrakis(1,3,5-trimethylphenyl)borate, tetrakis(4-fluorophenyl)borate, tetrakis(pentafluorophenyl)borate, and tetrakis(4-trifluoromethylphenyl)borate. Organic anions include, for example, alkanoates (such as, for example, acetate, propionate, and butanoate), benzoate, fumarate, maleate, tartrate, ascorbate, benzenesulfonate, toluenesulfonate, and citrate. In some embodiments, the pharmaceutically acceptable salt is free of unsubstituted or substituted tropolone.

In certain implementations, an ammonium salt may be formed by protonation of a compound of Formula I, wherein $R^1$ and $R^2$ are independently selected from a hydrogen atom and an alkyl group, with an inorganic acid, an organic acid, or a combination of an inorganic acid and an organic acid. In another embodiment, an ammonium salt may be formed by alkylation of a compound of Formula I, wherein $R^1$ and $R^2$ are independently selected from a hydrogen atom and an alkyl group, with an alkylating agent. In yet another embodiment, an ammonium salt may be formed by an ion exchange or metathesis reaction with a previously formed ammonium salt.

In some embodiments, $R^1$ includes an alkyl group and $R^2$ is $C(O)R^3$, where $R^3$ includes an alkyl group. In certain embodiments, $R^1$ includes an alkyl group having from about one to about four carbon atoms, and $R^3$ includes an alkyl group having from about four to about sixteen carbon atoms. In some embodiments, $R^1$ includes a methyl group, and $R^3$ includes an alkyl group having seven, eight, or nine carbon atoms. In some embodiments, the dental composition includes a compound of Formula II, Formula III, or Formula IV below.

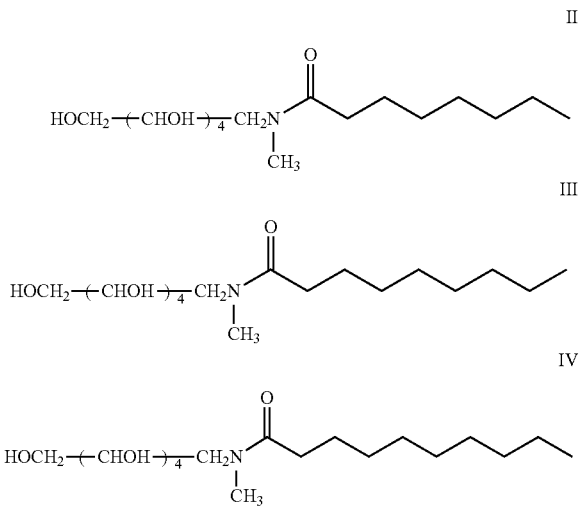

Disclosed aqueous liquid compositions 108 can include not greater than 5 wt-% of one or more surfactants based on the total weight of the composition, not greater than 4.5 wt-% of one or more surfactants based on the total weight of the composition, or not greater than 4 wt-% of one or more surfactants based on the total weight of the composition. In some embodiments, disclosed composition can include not less than 0.5 wt-% of one or more surfactants based on the total weight of the composition, not less than 0.4 wt-% of one or more surfactants based on the total weight of the composition, or not less than 0.3 wt-% of one or more surfactants based on the total weight of the composition.

The polymers used in forming the aqueous liquid 108 can be produced by polymerizing the above-described monomers by conventional polymerization methods. Typical polymerization methods that can be used include thermal and/or photochemical as well as bulk and solution polymerization.

In some embodiments, the viscosity modifier for the aqueous liquid 108 is a polysaccharide such as, for example, methyl cellulose, carboxymethyl cellulose, hydroxypropyl cellulose, hydroxyethyl cellulose, hydroxypropyl methyl cellulose, gellan gum, agarose, carrageenan, and mixtures and combinations thereof. In some embodiments, the aqueous liquid 108 may optionally further include a gelation initiator or promoter such as a monovalent or a divalent salt.

In some embodiments, the viscosity modifier for the aqueous liquid 108 is a silica compound. Suitable silica compounds include, but are not limited to, fumed or precipitated silicas such as those available under the trade designation AEROSIL from Evonik Industries, Parsippany, N.J., and CAB-O-SIL from Cabot Corp, Alpharetta, Ga. In some embodiments, which are not intended to be limiting, the aqueous liquid 108 includes not greater than about 3 wt %, or not greater than 2 wt %, or not greater than 1 wt %, of a silica-containing viscosity modifier.

In some embodiments, the viscosity modifier is present in an amount sufficient to cause the aqueous liquid 108 to form a gel, which in the present application refers to a flexible, viscous, liquid colloidal material that tends to cling to the dental appliance 100 such that a substantial portion of the gel remains in the tooth retaining cavities 104 until displaced by the teeth of the patient. In some embodiments, the gel is capable of swelling on contact with body fluids in the mouth, (or in fluids similar to body fluids such as physiological saline), but does not dissolve in water. The gels are substantially continuous, i.e., lacking a cellular or void structure (although minor defects such as entrapped air bubbles or fractures may be present), and thus generally are in a solid or semi-solid form. The term gel is used regardless of the state of hydration.

In some embodiments, the gel has a viscosity selected to prevent rapid drainage of the aqueous liquid from the tooth-retaining cavities 104 of the polymeric shell 102 when the dental appliance 100 being inserted into the mouth of the patient and the tooth retaining cavities 104 are positioned to overlie the teeth of the patient. For example, suitable drainage-resistant aqueous liquids with gel-like properties have been found to have a viscosity of about 0.001 Pa*s at shear rate 1/s to about 10 Pa*s at shear rate 1/s, at room temperature. In other embodiments, the gel has a viscosity selected to ease insertion of the dental appliance 100 into the mouth of the patient, or to ease positioning of the dental appliance 100 over the teeth of the patient. For example, aqueous liquids suitable for ease of dental appliance insertion are gels with a viscosity of about 0.001 Pa*s at shear rate 1/s to about 10 Pa*s at shear rate 1/s, at room temperature.

In various embodiments, the viscosity modifier in the aqueous liquid 108 is present at about 0.1 parts by weight to about 60 parts by weight.

In various embodiments, the aqueous liquid 108 in the system 10 further includes a tooth re-mineralizing agent alone or in combination with one or more minerals that may be useful or beneficial for ingestion or oral health.

Illustrative optional minerals that can be included in disclosed compositions of the aqueous liquid 108 can include calcium (Ca), phosphorus (P), magnesium (Mg), iron (Fe), strontium (Sr), zinc (Zn), potassium (K), or combinations thereof. In some embodiments, which are not intended to be limiting, some minerals can be provided by including magnesium chloride ($MgCl_2$), calcium chloride ($CaCl_2$)), strontium chloride, zinc chloride, zinc gluconate, potassium nitrate, potassium phosphate dibasic ($KH_2PO_4$), or combinations thereof.

In some embodiments, calcium and phosphate salts provide continuous opportunity for re-mineralization of tooth enamel, which can reverse or diminish the tooth decay process.

For example, in some embodiments, suitable tooth re-mineralizing agents include, but are not limited to, calcium compounds including $Ca^{2+}$ ions. Suitable calcium compounds include, but are not limited to, calcium chloride, calcium carbonate, calcium caseinate, calcium chloride, calcium citrate, calcium glubionate, calcium gluceptate, calcium glycerophosphate, calcium gluconate, calcium hydroxide, calcium hydroxyapatite, calcium lactate, calcium oxalate, calcium oxide, calcium pantothenate, calcium phosphate, calcium polycarbophil, calcium propionate, calcium pyrophosphate, calcium sulfate, and mixtures and combinations thereof. These compounds have been found to minimize demineralization of calcium hydroxyapatite at the surface of the tooth of a patient.

In some embodiments, the tooth re-mineralizing compounds include phosphate compounds. Suitable phosphate compounds include, but are not limited to, aluminum phosphate, bone phosphate, calcium phosphate, calcium orthophosphate, calcium phosphate dibasic anhydrous, calcium phosphate-bone ash, calcium phosphate dibasic dihydrate, calcium phosphate dibasic anhydrous, calcium phosphate dibasic dihydrate, calcium phosphate tribasic, dibasic calcium phosphate dihydrate, dicalcium phosphate, neutral calcium phosphate, calcium orthophosphate, tricalcium phosphate, precipitated calcium phosphate, tertiary calcium phosphate, whitlockite, magnesium phosphate, potassium phosphate, dibasic potassium phosphate, dipotassium hydrogen orthophosphate, dipotassium monophosphate, dipotassium phosphate, monobasic potassium phosphate, potassium acid phosphate, potassium biphosphate, potassium dihydrogen orthophosphate, potassium hydrogen phosphate, sodium phosphate, anhydrous sodium phosphate, dibasic sodium phosphate, disodium hydrogen orthophosphate, disodium hydrogen orthophosphate dodecahydrate, disodium hydrogen phosphate, disodium phosphate, and mixtures and combinations thereof.

In some embodiments, the calcium compounds, phosphate compounds, or both, are present in the aqueous liquid 108 in an amount sufficient such that the aqueous liquid 108 is saturated with at least one of $Ca^{2+}$ ions and $PO_4^{3-}$ ions. In some embodiments, an aqueous liquid 108 saturated in at least one of calcium ion or phosphate ion can substantially reduce or prevent demineralization, or enhance remineralization, or both, on the surface of the teeth of the patient.

In various embodiments, the tooth re-mineralizing agent in the aqueous liquid 108 is present at up to about 1 part by weight, or up to about 2 parts by weight, or up to about 5 parts by weight.

In some embodiments, disclosed compositions of the aqueous liquid 108 can include one or more preservatives to render the composition microbiologically stable, to increase the microbiological stability thereof, or some combination thereof. In some embodiments, useful preservatives include those that work at a neutral pH, do not detrimentally affect taste, are edible, are effective against a broad spectrum of pathogens, or combinations thereof. Specific illustrative useful preservatives can include preservatives available under the trade designation GEOGARD, which are commercially available from Lonza (Basel, Switzerland), as well as salicylic acid, benzyl alcohol, sodium benzoate, potassium sorbate, parabens, natural preservatives, polyglyceryl esters, monolaurin, 1,2 octanediol, caprylic/capric triglycerides, dehydroacetic acid (DHA), aloe vera, potassium sorbate, cetylpyridinium chloride (CPC), polyhexamethylene biguanide (PHMB), chlorhexidine gluconate (CHG), vitamin E, triethyl citrate, ethylenediaminetetraacetic acid (EDTA), for example.

Disclosed compositions of the aqueous liquid 108 can have varied properties. In some embodiments, disclosed compositions can be described by the pH thereof, the viscosity thereof, the stability thereof, various other properties, or combinations thereof.

In various embodiments, the aqueous liquid 108 in the system 10 has a pH suitable for use in the mouth of a patient, and may be selected to aid in neutralizing oral acids from food and bacteria present in the mouth of the patient. In various embodiments, for example, the aqueous liquid is buffered to have a pH of about 4.5 to about 9.5, or about 6.0 to about 8.0 (±0.1), or about 7.1 to about 7.35, or about 7.1. The composition can naturally have such a pH or can be buffered to have a pH in a useful, e.g., a "neutral" range.

In some embodiments, disclosed compositions can have desired stability properties. The stability of a composition can include microbiological stability, physical stability, or combinations thereof. In some embodiments, disclosed compositions are microbiologically stable for at least 6 months, in some embodiments 1 year, in some embodiments greater than 2 years.

In some embodiments, the aqueous liquid includes a buffering agent to maintain a desired pH range. Suitable buffering agents include, but are not limited to phosphates, carbonates, citrates, and mixtures and combinations thereof. In one embodiment, a suitable phosphate compound is $Na_2HPO_4$. In another embodiment, a water soluble polymer may be selected alone or in combination with the above buffering agents to provide both viscosity modification and buffering to maintain the pH of the aqueous liquid within a selected range.

In various embodiments, the aqueous liquid 108 includes about 40 parts by weight to about 95 parts by weight of a buffering agent, or up to about 98 parts by weight.

Disclosed compositions of the aqueous liquid 108 can also optionally include additional components such as, for example, sweeteners, humectants, mineral salts, buffering components, flavorants, preservative agents, or combinations thereof. Other optional beneficial ingredients can also be included at appropriate levels such as, aloe vera (multibenefit), folic acid (related to B12), hyaluronic acid (lubricating, healthy skin), ceramides (healthy skin), arginine, betaines or oxygenated glycerol triesters, vitamin E (antioxidant and preservative), vitamin B12 (healthy skin, etc.), EDTA, cetyl pyridinium chloride, chlorhexidine, other antiseptics, and combinations thereof.

In some embodiments, the aqueous liquid 108 of the system 10 further includes 0.1 parts by weight to about 10 parts by weight of a flavoring agent. Suitable flavoring agents may vary widely, but particularly useful flavoring agents have a pleasant taste and do not metabolize to acids at the surface of the tooth. Examples of suitable flavoring agents include, but are not limited to, polyol sugar alcohols such as xylitol, erythritol, glycerol, sorbitol and mixtures and combinations thereof.

In some embodiments, suitable flavorants include, but are not limited to, peppermint, strawberry, butter, vanilla, coconut, almond, bubble gum, berry, fruit punch, butterscotch, caramel, or combinations thereof. In some embodiments, some flavorants, e.g., mint, citrus, etc. can also be advantageous because they stimulate salivary production when utilized in compositions. Artificial sweeteners may also be used (stevia, aspartame, sucralose, neotame, acesulfame potassium (Ace-K), saccharin, and advantame, for example). In some embodiments, disclosed compositions can include one or more sweeteners including for example, non-cariogenic polyols, or sugar substitutes (e.g., sucralose). In some embodiments, disclosed compositions can include non-cariogenic polyol sweeteners such as xylitol, sorbitol, maltitol, erythritol, isomalt, or combinations thereof. In compositions that include optional sweeteners, the sweetener can be present in an amount that is not less than 2.5 wt % based on the total weight of the composition or not less than 1 wt % based on the total weight of the composition. In some embodiments, an optional sweetener can be present in an amount that is not greater than 20 wt % based on the total weight of the composition or not greater than 15 wt %, based on the total weight of the composition.

In some embodiments, the aqueous liquid 108 in the system 10 may optionally include dyes or pigments to provide a desired color that may be, for example, decorative or selected to improve the appearance of the teeth of the patient.

In some embodiments, disclosed compositions of the aqueous liquid 108 can prevent, inhibit, disrupt the formation or maintenance of a biofilm in an area contacted with the composition. The area contacted can be in vivo or in vitro. In some embodiments, a composition can prevent, inhibit, disrupt the formation or maintenance of a biofilm in a mouth of a user where the composition was applied to the mouth, for example via spraying the composition into the mouth when compared to a mouth without the composition applied thereto.

In some embodiments, the aqueous liquid 108 can prevent, inhibit, disrupt the formation or maintenance of a biofilm in a container in which a biofilm exists and the composition was applied to the container via pouring, spraying, and the like, when compared to a container without the composition applied thereto. Preventing, inhibiting, disrupting, or some combination thereof the formation or maintenance of biofilms can be measured using a modified version of the MBEC assay (described in ASTM E2799), which measures disruption of *Strep mutans* biofilms grown on special pegs in a microtiter plate. The biofilms growing on the pegs are treated by periodic submersion into test materials, followed by washing in saliva and water. The biofilm remaining on each peg following treatment is quantified by measuring the amount of fluorescently labeled bacteria that eluted from the pegs at the end of the treatment cycles. In some embodiments, disclosed compositions can affect the buildup of plaque in an area contacted by the composition. The area contacted can be in vivo or in vitro. In some embodiments, a composition can decrease plaque buildup on at least one tooth in a mouth of a user where the composition was applied to the mouth, for example via spraying the composition into the mouth when compared to a mouth without the composition applied thereto. In some embodiments, a composition can decrease plaque buildup in a container in which plaque can develop and the composition was applied to the container via pouring, spraying, etc. when compared to a container without the composition applied thereto. Decreasing plaque buildup can be measured by a variety of methods in vivo including for example plaque scoring, dyeing of plaque, and the like.

In some embodiments, disclosed compositions of the aqueous liquid 108 can affect lubricity or lubriciousness of an area contacted by the composition. Lubricity can be beneficial to ease insertion and removal of the dental appliance 100 into the mouth and over the teeth of the patient while not negatively affecting the forces applied by the dental appliance in specific locations to gradually move the teeth into the new configuration. In some embodiments, a composition can maintain or increase lubricity. In some embodiments, a composition can provide lubricating properties to a mouth to the same degree or greater that saliva can, for example. Lubricity or the ability to provide lubricating properties can be measured by the friction coefficient relative to a suitable substrate. A low friction coefficient (comparable to saliva) is desired.

In some embodiments, disclosed compositions of the aqueous liquid 108 can combine numerous desired benefits such as aesthetic appearance, remineralization, lubrication, caries prevention, moisturization, pH buffering to neutralize potential acids generated by the oral biofilm. Finding an ingestible biocompatible cosmetic aqueous liquid to achieve all of the desired benefits required significant experimental investigation, was non-trivial, and required more than routine optimization. Furthermore, some disclosed compositions also achieve desired physical stability (desirable product shelf life and commercial usefulness). Surprisingly some of these formulations also have anti-plaque property that may be demonstrated by in vitro anti-biofilm studies using *Streptococcus mutans*, a well-known biofilm-forming bacteria responsible for dental plaque.

In one example embodiment, the aqueous liquid 108 includes about 0.1 part by weight to about 60 parts by weight of a viscosity modifier chosen from polysaccharides, water compatible polymers, silica compounds, and mixtures and combinations thereof; about 40 parts by weight to about 95 parts by weight of a buffering agent; up to about 1 part by weight of a tooth re-mineralizing agent comprising a calcium compound; optionally about 0.1 parts by weight to about 10 parts by weight of a flavoring agent; and water. The aqueous liquid is substantially free of tooth whitening agents and fluoride, and wherein a refractive index of the aqueous liquid is greater than 1.3, or greater than 1.33, or greater than 1.34.

In another embodiment, aqueous liquid 108 includes 0.5 parts by weight to about 60 parts by weight of a water soluble polymer chosen from polyacrylic acid, polyethylene glycol, ethylene oxide/propylene oxide copolymers, and combinations thereof, about 40 parts by weight to about 95 parts by weight of a buffering agent; up to about 1 part by weight of a tooth re-mineralizing agent comprising a calcium compound; optionally about 0.1 parts by weight to about 10 parts by weight of a flavoring agent; and water. The aqueous liquid is substantially free of tooth whitening agents and fluoride, and wherein a refractive index of the aqueous liquid is greater than 1.3, or greater than 1.33, or greater than 1.34.

The shell 102 of the orthodontic appliance 100 is an elastic polymeric material that generally conforms to a patient's teeth, and may be transparent, translucent, or opaque. In some embodiments, the shell 102 is a clear or substantially transparent polymeric material that may include, for example, one or more of amorphous thermoplastic polymers, semi-crystalline thermoplastic polymers and transparent thermoplastic polymers. In some embodiments, the shell 102 includes a material chosen from polyurethane, polycarbonate, acrylic, polysulfone, polypropylene, polyester, copolyester, polypropylene/ethylene copolymer, cyclic olefin polymer/copolymer, poly-4-methyl-1-pentene or polyester/polycarbonate copolymer, styrenic polymeric materials, polyamide, polymethylpentene, polyetherketone and combinations thereof. In another embodiment, the shell 102 may be chosen from clear or substantially transparent semi-crystalline thermoplastic, crystalline thermoplastics and composites, such as polyamide, polyethylene terephthalate, polybutylene terephthalate, polyester/polycarbonate copolymer, polyolefin, cyclic olefin polymer, styrenic copolymer, polyetherimide, polvetherketone, polyethersulfone, polytrimethylene terephthalate, and mixtures and combinations thereof. In some embodiments, the shell 102 is a polymeric material chosen from polyethylene terephthalate, polyethylene terephthalate glycol (PETg), polycyclohexylenedimethylene terephthalate glycol, poly(meth)acrylates (which include polymethacrylates and polyacrylates), and mixtures and combinations thereof. One example of a commercially available material suitable as the elastic polymeric material for the shell 102, which is not intended to be limiting, is PETg. Suitable PETg resins can be obtained from various commercial suppliers such as, for example, Eastman Chemical, Kingsport, Tenn., SK Chemicals, Irvine, Calif.; DowDuPont, Midland. MIL Pacur, Oshkosh, Wis.; and Scheu Dental Tech, Iserlohn, Germany.

In some embodiments, the shell 102 may be made of a single polymeric material, or may include multiple layers of different polymeric materials.

In one embodiment, the shell 102 is a substantially transparent polymeric material. In this application the term substantially transparent refers to materials that pass light in the wavelength region sensitive to the human eye (about 400 nm to about 750 nm) while rejecting light in other regions of the electromagnetic spectrum. In some embodiments, the reflective edge of the polymeric material selected for the shell 102 should be above about 750 nm, just out of the sensitivity of the human eye.

The orthodontic appliance 100 may be made using a wide variety of techniques A plurality of cavities 104 may be formed in a substantially flat sheet of polymeric material to form the orthodontic appliance 100, wherein the cavities are configured to receive one or more teeth. The cavities 104 may be formed by any suitable technique, including thermoforming, laser processing, chemical or physical etching, and combinations thereof.

In another embodiment, the shell-like orthodontic dental appliance 100 may be formed using a three-dimensional (3D) printing process (e.g. additive manufacturing), such as stereolithography.

Figure 2:
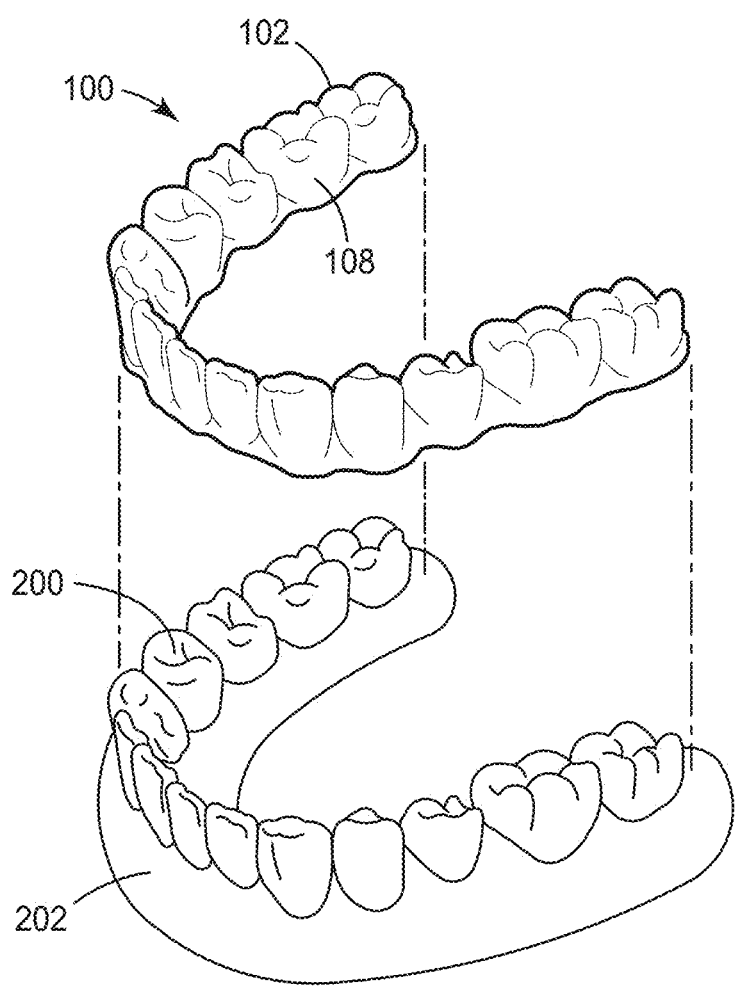
FIG. 2 is a schematic overhead perspective view of a method in which for using a dental alignment tray is placed in the mouth of a patient to overlie teeth.

Referring now to FIG. 2, the shell 102 of the orthodontic appliance 100 generally conforms to a patient's teeth 200, but is slightly out of alignment with the patient's initial maloccluded tooth configuration. In some embodiments, the shell 102 may be one of a group or a series of shells having substantially the same shape or mold, but which are formed from different materials to provide a different stiffness or resilience as needed to move the teeth of the patient. In this manner, in one embodiment, a patient or a user may alternately use one of the orthodontic appliances during each treatment stage depending upon the patient's preferred usage time or desired treatment time period for each treatment stage.

No wires or other means may be provided for holding the shell 102 over the teeth 200, but in some embodiments, it may be desirable or necessary to provide individual anchors on teeth with corresponding receptacles or apertures in the shell 102 so that the shell 102 can apply a retentive or other directional orthodontic force on the tooth which would not be possible in the absence of such an anchor.

The shells 102 may be customized, for example, for day time use and night time use, during function or non-function (chewing vs non-chewing), during social settings (where appearance may be more important) and nonsocial settings (where the aesthetic appearance may not be a significant factor), or based on the patient's desire to accelerate the teeth movement (by optionally using the more stiff appliance for a longer period of time as opposed to the less stiff appliance for each treatment stage).

For example, in one aspect, the patient may be provided with a clear orthodontic appliance that may be primarily used to retain the position of the teeth, and an opaque orthodontic appliance that may be primarily used to move the teeth for each treatment stage. Accordingly, during the day time, in social settings, or otherwise in an environment where the patient is more acutely aware of the physical appearance, the patient may use the clear appliance. Moreover, during the evening or night time, in non-social settings, or otherwise when in an environment where physical appearance is less important, the patient may use the opaque appliance that is configured to apply a different amount of force or otherwise has a stiffer configuration to accelerate the teeth movement during each treatment stage. This approach may be repeated so that each of the pair of appliances are alternately used during each treatment stage.

Referring again to FIG. 2, the orthodontic appliance 100 and the aqueous solution 108 form a dental alignment system. For example, a patient may be provided with a series of a plurality of incremental orthodontic appliances 100, each formed from the same or a different material, for each treatment stage of orthodontic treatment. The orthodontic appliances may be configured such that each successive member of the series incrementally repositions individual teeth 200 in an upper or lower jaw 202 of a patient from a maloccluded position to a desired non-occluded position. In some embodiments, the cavities 104 are configured such that selected teeth will be repositioned, while others of the teeth will be designated as a base or anchor region for holding the repositioning appliance in place as it applies the resilient repositioning force against the tooth or teeth intended to be repositioned.

Prior to placement of the elastic orthodontic appliance 100 over the teeth, the aqueous solution 108 is applied in some or all of the cavities 104 in the polymeric shell 102. The aqueous solution 108 is applied in the cavities 104 in an amount sufficient such that when the orthodontic appliance 100 is placed over the teeth, the aqueous solution occupies and remains in the air gap between the polymeric shell 102 and the teeth.

As noted above, in some embodiments the aqueous solution is a gel, and has a viscosity selected such that all or a substantial amount of the gel remains in the cavities 104 as the polymeric shell 102 is placed over the teeth and the teeth are inserted into the cavities 104. As the teeth enter the cavities 104, a portion of the gel is displaced, but sufficient gel remains to substantially fill the air gap between the polymeric shell 102 and the teeth. As noted above, in various embodiments the gel may be used to facilitate the insertion and placement of the polymeric shell 102 over the teeth.

In some embodiments, the aqueous solution 108 may be dispensed from a collapsible tube-like container, a syringe, or an applicator and manually applied to the cavities 104 prior to insertion of the polymeric shell 102 over the teeth. In another embodiment, an automatic dispenser may be used to dispense a controlled amount of the aqueous liquid 108 into the cavities 104.

Placement of the elastic dental appliance 100 over the teeth 200 applies controlled forces in specific locations to gradually move the teeth into the new configuration. Repetition of this process with successive dental appliances having different configurations eventually moves a patient's teeth through a series of intermediate configurations to a final desired configuration.

Figure 3:
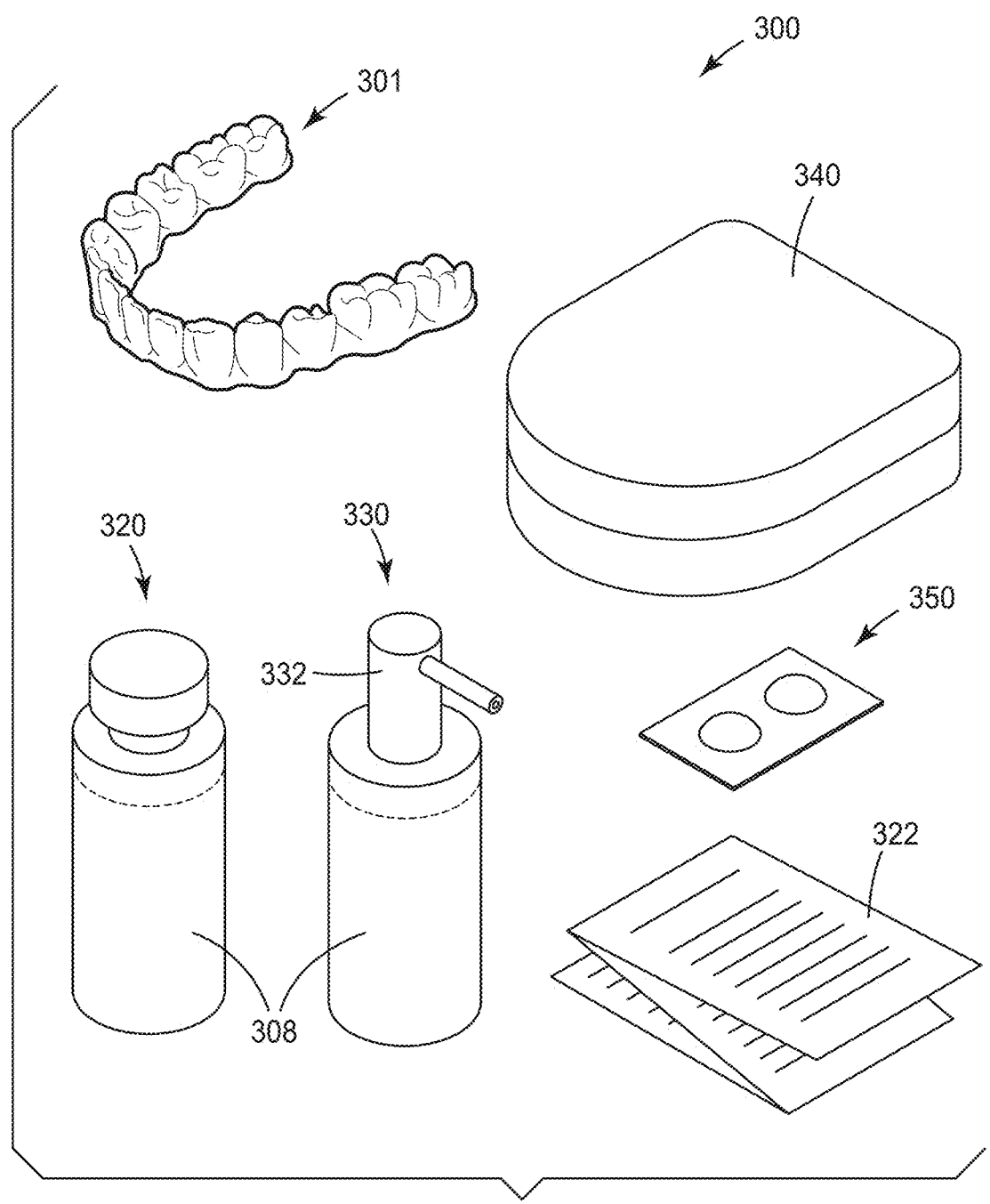
FIG. 3 is a schematic diagram of components of a kit including the dental appliance and cosmetic aqueous liquid.

Referring to FIG. 3, in various embodiments the system may be supplied in the form of a kit 300 including the dental appliance 301 and the aqueous solution 308. In one embodiment, the aqueous solution 308 may be supplied in a container 320 such as, for example, a squeezable bottle or a collapsible tube, along with instructions 322 for proper application to the dental appliance 301. In another embodiment, the aqueous solution 308 may be supplied in a dispenser 330, wherein the dispenser 330 includes for example, a syringe, a trigger-operated gun, or a pump 332 configured to dispense a predetermined amount of the aqueous solution 308 for each insertion of the dental appliance 301 into the mouth of the patient. In another embodiment, the dispenser 330 may be configured to automatically dispense a predetermined amount of the aqueous solution 308 for each insertion of the dental appliance 301. In another embodiment, the kit may optionally include additional items such as, for example, a storage case 340, which may serve as a holder or an automated cleaning apparatus for temporary storage of the dental appliance 301 while not the dental appliance is not in the mouth of the patient, liquid cleaning or disinfecting solutions or solid tablets 350 dissolvable in water for use with the storage case or automated cleaning apparatus, a charger for the automated dispenser or cleaning apparatus, instructions for use, and the like.

Figure 4:
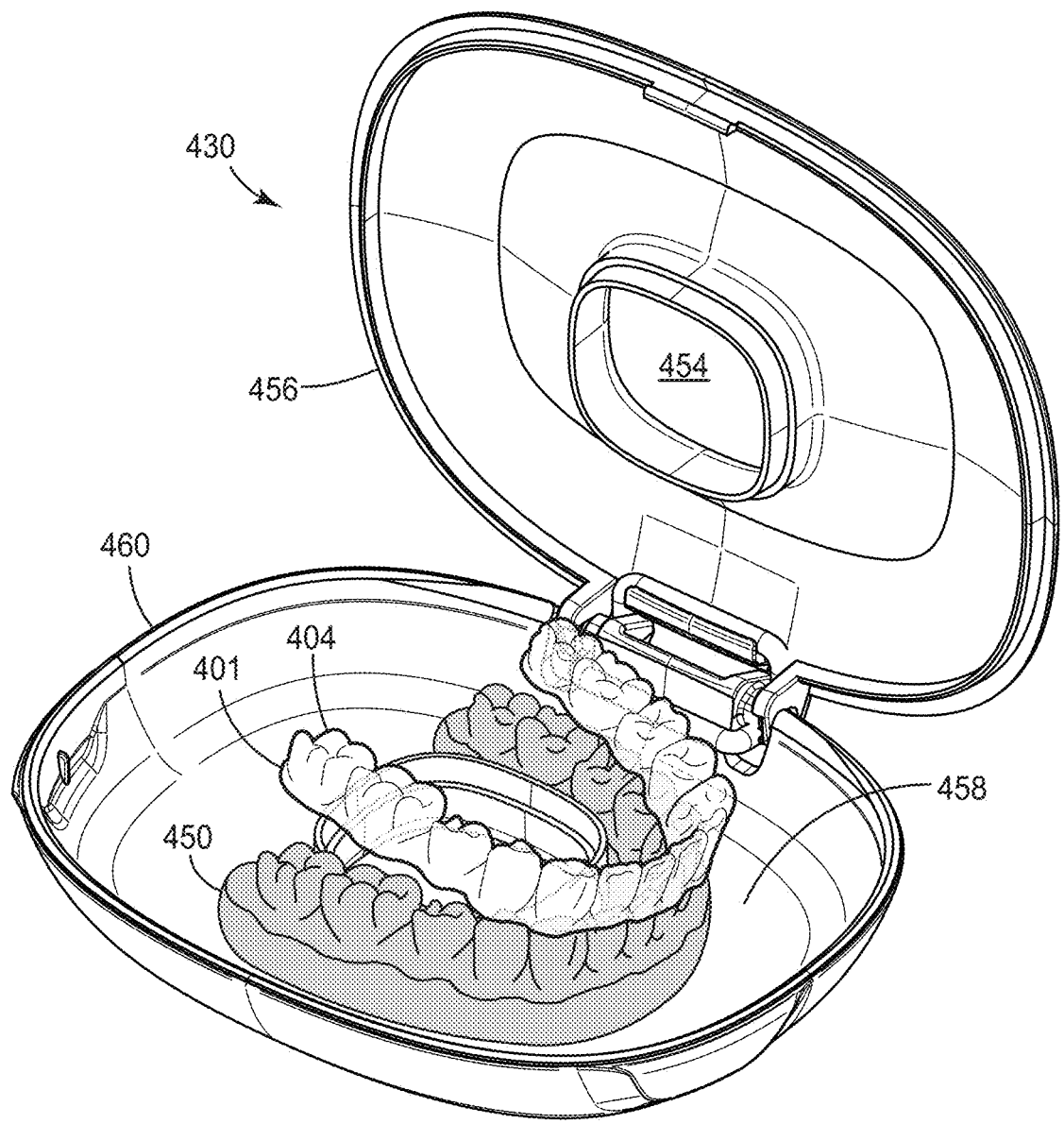
FIG. 4 is a schematic illustration of a reclosable storage unit and dispenser configured to hold a dental appliance and dispense a cosmetic aqueous liquid into the tooth-retaining cavities in the dental appliance.

As shown in FIG. 4, in one example embodiment a re-closable storage unit and dispenser 430 includes a foam applicator pad 450 shaped to hold a shell-like dental appliance 401 including tooth-retaining cavities 404. The storage unit and dispenser 430 further includes an opening 454 in a hinged cover 456. When an aqueous liquid (not shown in FIG. 4) is dispensed into, for example, a reservoir 458 in a bottom portion 460 of the dispenser 430, or directly on to the applicator pad 450, the aqueous liquid collects in the reservoir 458. The foam applicator pad 450 absorbs the aqueous liquid from the reservoir 458. When the cover 456 is closed and engages the bottom portion 460 of the dispenser 430, the dental appliance 401 is pressed against the foam applicator pad 450. The foam applicator pad 450 dispenses a predetermined measured amount of the aqueous liquid into the cavities 404 of the dental appliance 401.

The systems of the present disclosure will now be further described in the following non-limiting examples.

EXAMPLES

Four solutions were prepared as described in Table 1 below:

TABLE 1

| Component | Supplier | Address |
|---|---|---|
| Citric acid | Alfa Aesar | Tewksbury, MA, USA |
| Calcium dihydrogen phosphate hydrate | Alfa Aesar | Tewksbury, MA, USA |
| CARBOPOL 974PNF (polyacrylic acid) | Lubrizol | Cleveland, OH |
| Sodium hydrogen phosphate ($Na_2HPO_4$) | J. T. Baker | Center valley, PA |
| Xylitol | Roquette | Keokuk, IA |
| Triethanolamine | J. T. Baker | Center Valley, PA |
| NATROSOL 250HHX Pharm, hydroxy ethyl cellulose (HEC) | Ashland | Wilmington, DE, USA |
| KOLLIPHOR P407 (EO/PO copolymer) | BASF | Ludwishafen, Germany |
| PEG 3350 | Walgreens | Deerfield, IL | pH Testing pH testing was carried out on a standard pH meter after calibration. The pH meter was an ACCUMET model 15 pH meter from Fisher Scientific. The pH measurement was performed by inserting the pH probe into the solution, waiting for 2 minutes and recording the pH value. pH values are listed in the example tables.

Solution Preparation and Application

The solutions were prepared by mixing necessary ingredients to provide certain desired functions, such as wetting to teeth, providing pH buffering to neutralize potential acids generated by the oral biofilm, providing calcium phosphate to mimic saliva, and some flavor. Xylitol was added for flavor and caries prevention. The solutions in the examples below contain a water soluble polymer, phosphate buffer, xylitol, calcium phosphate and water for cosmetic application in a clear tray aligner to provide wetting and reduce light scattering, which can reduce the clear aligner polymer film visibility on the teeth of the patient.

Buffer Solution Preparation pH 7.3 Buffer 3.84 grams of Citric Acid was dissolved in 200 mL of DI water. 28.4 grams of $Na_2HPO_4$ was dissolved in 1000 mL of DI water. Once both solutions were made, 130 mL of the Citric Acid solution was added to the 1000 mL of $Na_2HPO_4$ solution. The pH of the final combined solution was 7.33.

pH 6.4 Buffer 1.92 grams of Citric Acid was dissolved in 100 mL of DI water, and this step was repeated to create 200 mL of Citric Acid solution. 14.2 grams of $Na_2HPO_4$ was dissolved in 500 mL of DI water. Once both solutions are made, 335 mL of the $Na_2HPO_4$ solution was added to 150 mL of the Citric Acid solution. The pH of the final solution was 6.39.

CARBOPOL Polymer Buffer

DI water was added into a glass jar, followed by triethanolamine and disodium hydrogen phosphate, and the components were mixed well to form a solution. CARBOPOL 974P NF was then added into the glass jar, and mixed well to form a viscous solution. The detailed formulation of the CARBOPOL polymer buffer is set forth in Table 2 below, and the pH was measured as 7.0.

TABLE 2

| Component | Mass (grams) | Mass % |
|---|---|---|
| DI water | 773 | 96.38 |
| CARBOPOL 974PNF | 8 | 1.00 |
| triethanolamine | 10 | 1.25 |
| Na2HPO4 | 11 | 1.37 |
| total | 802 | 100 |

Aligner Aqueous Liquid Preparation

Various examples of aqueous liquids are set forth below. To make the liquids, the chemical components listed in the Tables below were added into a glass jar and mixed well to form solutions. The pH of different solutions was measured with a pH meter and a probe.

Aqueous Liquid Example 1

The formulation of Aqueous Liquid Example 1 is set forth in Table 3 below.

TABLE 3

| Component | Mass (grams) |
|---|---|
| CARBOPOL Polymer Buffer solution pH 7.0 | 49 |
| pH 7.33 buffer | 49 |
| xylitol | 1.95 |
| calcium dihydrogen phosphate hydrate | 0.05 |
| total | 100 |

The pH of Aqueous Liquid Example 1 was 7.11.

Aqueous Liquid Example 2

The formulation of Aqueous Liquid Example 2 is set forth in Table 4 below.

TABLE 4

| Component | Mass (grams) |
| --- | --- |
| PEG3350 | 20 |
| pH 6.40 buffer | 30 |
| xylitol | 1 |
| calcium dihydrogen phosphate hydrate | 0.025 |
| total | 50 |

The pH of Aqueous Liquid Example 2 was 7.17.

Aqueous Liquid Example 3

The formulation of Aqueous Liquid Example 3 is set forth in Table 5 below.

TABLE 5

| Component | Mass (grams) |
| --- | --- |
| KOLLIPHOR P407 | 10 |
| pH 7.33 buffer | 84.975 |
| xylitol | 5 |
| calcium dihydrogen phosphate hydrate | 0.025 |
| total | 100 |

The pH of Aqueous Liquid Example 3 was 7.33.

Aqueous Liquid Example 4

The formulation of Aqueous Liquid Example 4 is set forth in Table 6 below.

TABLE 6

| Component | Mass (grams) |
| --- | --- |
| HFC Natrosol 250HHX pharm | 0.8 |
| pH 7.33 buffer | 94.175 |
| xylitol | 5 |
| calcium dihydrogen phosphate hydrate | 0.025 |
| total | 100 |

The pH of Aqueous Liquid Example 4 was 7.25.

The Aqueous Liquids were inserted into clear dental aligner trays and installed on typodont models with and without the solutions. The solutions reduced the appearance of dark areas near the occlusal edges and cusp tips, which made the aligner trays less noticeable.

EMBODIMENTS

Embodiment A

A system, comprising:
a dental appliance comprising a polymeric shell with a plurality of cavities for receiving one or more teeth; and
a biocompatible cosmetic aqueous liquid in the cavities of the polymeric shell of the dental appliance, the aqueous liquid comprising:
  a viscosity modifier chosen from a water compatible polymer, a polysaccharide, a silica compound, and mixtures and combinations thereof,
  a tooth re-mineralizing agent, and
  water,
wherein the aqueous liquid is substantially free of tooth whitening agents and fluoride, and wherein the aqueous liquid has a refractive index of greater than 1.3 at room temperature.

Embodiment B

The system of Embodiment A, wherein the polymeric shell is a polymeric material chosen from polyurethane, polyester, polyethylene terephthalate, polyethylene terephthalate glycol, poly cyclohexylenedimethylene terephthalate glycol, poly(meth)acrylates and mixtures and combinations thereof.

Embodiment C

The system of Embodiments A and B, wherein the refractive index of the aqueous liquid is greater than 1.33.

Embodiment D

The system of Embodiments A and B, wherein the refractive index of the aqueous liquid is greater than 1.34.

Embodiment E

The system of any of Embodiments A to D, wherein the aqueous liquid has a pH of about 6.0 to about 8.0.

Embodiment F

The system of any of Embodiments A to D, wherein the aqueous liquid has a pH of about 7.1 to about 7.35.

Embodiment G

The system of any of Embodiments A to F, wherein the polysaccharide is chosen from ethyl cellulose, methyl cellulose, carboxymethyl cellulose, hydroxyethyl cellulose, hydroxypropyl cellulose, xanthan gum, agarose, carrageenan, and mixtures and combinations thereof.

Embodiment H

The system of Embodiment G, wherein the polysaccharide is hydroxyethyl cellulose.

Embodiment I

The system of Embodiment G, wherein the polysaccharide is ethyl cellulose.

Embodiment J

The system of any of Embodiments A to I, wherein the water compatible polymer comprises a water-soluble polymer.

Embodiment K

The system of Embodiment J, wherein the water soluble polymer is chosen from polyacrylic acid and salts thereof, polyethylene glycol, ethylene oxide/propylene oxide copolymers, and mixtures and combinations thereof.

Embodiment L

The system of any of Embodiments A to K, wherein the silica compound comprises a fumed silica.

Embodiment M

The system of any of Embodiments A to L, wherein the composition comprises not greater than 3 wt % of a silica-containing viscosity modifier.

Embodiment N

The system of any of Embodiments A to M, wherein the aqueous liquid further comprises a buffering agent chosen from phosphate, carbonate, citrate, and mixtures and combinations thereof.

Embodiment O

The system of Embodiment N, wherein the phosphate compound is $Na_2HPO_4$.

Embodiment P

The system of any of Embodiments N and O, wherein the buffering agent further comprises a water soluble polymer.

Embodiment Q

The system of any of Embodiments A to P, wherein the tooth re-mineralizing agent comprises a calcium compound.

Embodiment R

The system of Embodiment Q, wherein the calcium compound comprises calcium phosphate.

Embodiment S

The system of any of Embodiments A to R, wherein the aqueous liquid further comprises a flavoring agent.

Embodiment T

The system of Embodiment S, wherein the flavoring agent is a polyol sugar alcohol.

Embodiment U

The system of Embodiment T, wherein the polyol sugar alcohol is chosen from xylitol, erythritol, glycerol, sorbitol and mixtures and combinations thereof.

Embodiment V

The system of Embodiment U, wherein the polyol sugar alcohol comprises xylitol.

Embodiment W

The system of any of Embodiments A to V, wherein the aqueous liquid comprises a surfactant of Formula I:

$$HOCH_2-(CHOH)_n-CH_2NR^1R^2 \quad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group;
and n is an integer from about 2 to about 5.

Embodiment X

The system of Embodiment W, wherein the surfactant of Formula I is present in the aqueous liquid at not greater than 4 wt %, based on the total weight of the composition.

Embodiment Y

The system of any of Embodiments A to X, wherein the aqueous liquid further comprises sweeteners, humectants, mineral salts, buffering components, flavorants, preservative agents, or combinations thereof.

Embodiment Z

The system of any of Embodiments A to Y, wherein the aqueous liquid further comprises aloe vera, folic acid, hyaluronic acid, ceramides, arginine, betaines or oxygenated glycerol triesters, vitamin E, vitamin B12, EDTA, cetyl pyridinium chloride, chlorhexidine, other antiseptics, or combinations thereof.

Embodiment AA

The system of any one of Embodiments A to Z, wherein the aqueous liquid is sprayable.

Embodiment BB

The system of any one of Embodiments A to Z, wherein the aqueous liquid prevents, inhibits, disrupts, or any combination thereof the formation or maintenance of a biofilm in an area contacted with the aqueous liquid.

Embodiment CC

A method of preventing, inhibiting, disrupting, or any combination thereof the formation or maintenance of a biofilm in an oral tissue, the method comprising contacting an oral tissue with the aqueous liquid according to any of Embodiments A to CC.

Embodiment DD

The system of any one of Embodiments A to BB, wherein at least one cavity in the polymeric shell of the dental appliance is configured to adjust a tooth from a maloccluded position to a desired position.

Embodiment EE

A system, comprising:
a dental appliance comprising a polymeric shell with a plurality of cavities for receiving one or more teeth, wherein the polymeric shell is a polymeric material chosen from polyurethane, polyester, polyethylene terephthalate, polyethylene terephthalate glycol, poly cyclohexylenedimethylene terephthalate glycol, poly (meth)acrylates and mixtures and combinations thereof; and a biocompatible cosmetic aqueous liquid in at least some of the cavities of the polymeric shell of the dental appliance, the aqueous liquid comprising:
about 0.1 parts by weight to about 60 parts by weight of a viscosity modifier chosen from polysaccharides, water compatible polymers, silica compounds, and mixtures and combinations thereof;
about 40 parts by weight to about 95 parts by weight of a buffering agent comprising a phosphate compound;
up to about 1 part by weight of a tooth re-mineralizing agent comprising a calcium compound; and
water;
wherein the aqueous liquid is substantially free of tooth whitening agents and fluoride, and wherein a refractive index of the aqueous liquid is greater than 1.3.

Embodiment FF

The system of Embodiment EE, wherein the refractive index of the aqueous liquid is greater than 1.33.

Embodiment GG

The system of Embodiment EE, wherein the refractive index of the aqueous liquid is greater than 1.34.

Embodiment HH

The system of any of Embodiments EE to GG, wherein the water compatible polymer is a water soluble polymer chosen from polyacrylic acid, polyethylene glycol, ethylene oxide/propylene oxide copolymers, and combinations thereof, and wherein the water soluble polymer is present in the aqueous liquid at about 0.5 parts by weight to about 60 parts by weight.

Embodiment II

The system of any of Embodiments EE to HH, wherein the silica compound comprises not greater than 3 wt % of a viscosity modifier comprising a fumed silica.

Embodiment JJ

The system of any of Embodiments EE to II, wherein the aqueous liquid has a pH of about 6.0 to about 8.0.

Embodiment KK

The system of any of Embodiments EE to II, wherein the aqueous liquid has a pH of about 7.1 to about 7.35.

Embodiments LL

The system of any of Embodiments EE to KK, wherein the aqueous liquid has a viscosity of about 0.001 Pa*s at shear rate 1/s to about 10 Pa*s at shear rate 1/s, at 20° C.

Embodiment MM

The system of any of Embodiments EE to LL, wherein the aqueous liquid further comprises about 0.1 part by weigh to about 10 parts by weight of a flavoring agent comprising a polyol sugar alcohol.

Embodiment NN

The system of any of Embodiment MM, wherein the polyol sugar alcohol comprises xylitol.

Embodiment OO

The system of any of Embodiments EE to NN, wherein the calcium compound comprises calcium phosphate.

Embodiment PP

The system of any of Embodiments EE to OO, wherein the polymeric shell and the aqueous liquid transmit at least 60% of incident light with a wavelength of about 400-750 nm.

Embodiment QQ

The system of any of Embodiments EE to PP, wherein the aqueous liquid is substantially transparent to visible light with a wavelength of 400-750 nm.

Embodiment RR

The system of any of Embodiments EE to QQ, wherein the aqueous liquid comprises not greater than 4 wt % of a surfactant of formula I, based on the total weight of the composition:

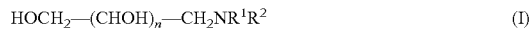

$$HOCH_2-(CHOH)_n-CH_2NR^1R^2 \qquad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group;
and n is an integer from about 2 to about 5.

Embodiment SS

The system of any one of Embodiments EE to RR, wherein the aqueous liquid is sprayable.

Embodiment TT

The system of any one of Embodiments EE to SS, wherein the aqueous liquid prevents, inhibits, disrupts, or any combination thereof the formation or maintenance of a biofilm in an area contacted with the aqueous liquid.

Embodiment UU

A method of preventing, inhibiting, disrupting, or any combination thereof the formation or maintenance of a biofilm in an oral tissue, the method comprising: contacting an oral tissue with the aqueous liquid according to any of Embodiments EE to TT.

Embodiment VV

The system of any one of Embodiments EE to UU, wherein at least one cavity in the polymeric shell of the dental appliance is configured to adjust a tooth from a maloccluded position to a desired position.

Embodiment WW

A method in which a tooth is inserted in a cavity in a polymeric shell of a dental appliance to adjust the tooth from a maloccluded position to a desired position, the method comprising applying in the cavity a biocompatible cosmetic aqueous liquid comprising a viscosity modifier chosen from polysaccharides, water compatible polymers, silica compounds and mixtures and combinations thereof; a tooth re-mineralizing agent; and water; wherein the aqueous liquid is substantially free of tooth whitening agents and fluoride, and wherein a refractive index of the aqueous liquid is greater than 1.3.

Embodiment XX

The method of Embodiment WW, wherein the refractive index of the aqueous liquid is greater than 1.33.

Embodiment YY

The method of Embodiments WW and XX, wherein the water compatible polymer is a water soluble polymer chosen from polyacrylic acid, polyethylene glycol, ethylene oxide/propylene oxide copolymers, and combinations thereof, and wherein the water soluble polymer is present in the biocompatible aqueous liquid at about 0.5 parts by weight to about 60 parts by weight.

Embodiment ZZ

The method of any of Embodiments WW to YY, wherein the silica compound comprises a fumed silica.

Embodiment AAA

The method of any of Embodiments WW to ZZ, wherein the aqueous liquid has a pH of about 7.1 to about 7.35.

Embodiment BBB

The method of any of Embodiments WW to AAA, wherein the aqueous liquid has a viscosity of about 0.001 Pa*s at shear rate 1/s to about 10 Pa*s at shear rate 1/s, at 20° C.

Embodiment CCC

The method of any of Embodiments WW to BBB, wherein the aqueous liquid further comprises about 0.1 parts by weight to about 10 parts by weight of a flavoring agent comprising xylitol.

Embodiment DDD

The method of any of Embodiments WW to CCC, wherein the calcium compound comprises calcium phosphate.

Embodiment EEE

The method of any of Embodiments WW to DDD, wherein the polymeric shell and the aqueous liquid transmit at least 60% of incident light with a wavelength of about 400-750 nm.

Embodiment FFF

The method of any of Embodiments WW to EEE, wherein the aqueous liquid is substantially transparent to visible light with a wavelength of 400-750 nm.

Embodiment GGG

The method of any of Embodiments WW to FFF, wherein the aqueous liquid comprises not greater than 4 wt % of a surfactant of formula I, based on the total weight of the composition:

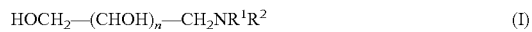

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; and n is an integer from about 2 to about 5.

Embodiment HHH

The method of any of Embodiments WW to GGG, wherein the biocompatible aqueous liquid comprises:
about 0.1 parts by weight to about 60 parts by weight of a viscosity modifier chosen from polysaccharides, water soluble polymers, water-dispersible polymers, fumed silica, and mixtures and combinations thereof;
about 40 parts by weight to about 95 parts by weight of a buffering agent comprising a phosphate compound;
up to about 1 part by weight of a tooth re-mineralizing agent comprising a calcium compound;
about 0.1 parts by weight to about 10 parts by weight of a flavoring agent; and
water.

Embodiment III

The method of any of Embodiments WW to HHH, wherein the polymeric shell is a polymeric material chosen from polyethylene terephthalate, polyethylene terephthalate glycol, poly cyclohexylenedimethylene terephthalate glycol, and mixtures and combinations thereof.

Embodiment JJJ

A kit, comprising:
a dental appliance comprising a polymeric shell with a plurality of cavities for receiving one or more teeth; and
a biocompatible cosmetic aqueous liquid comprising:
a viscosity modifier chosen from polysaccharides, water compatible polymers, silica compounds, and mixtures and combinations thereof;
a tooth re-mineralizing agent; and
water;
wherein the aqueous liquid is substantially free of tooth whitening agents and fluoride, and wherein a refractive index of the aqueous liquid is greater than 1.3.

Embodiment KKK

The kit of Embodiment JJJ, further comprising an applicator for applying the aqueous liquid to the dental appliance.

Embodiment LLL

The kit of Embodiments JJJ and KKK, further comprising instructions for applying the aqueous liquid to the dental appliance.

Embodiment MMM

The kit of any of Embodiments JJJ to LLL, further comprising a re-closable tray for retaining the polymeric shell.

Embodiment NNN

The kit of any of Embodiments JJJ to MMM, further comprising a dispenser to dispense the aqueous liquid into the dental appliance.

Embodiment OOO

The kit of Embodiment NNN, wherein the dispenser is automated.

Embodiment PPP

The kit of any of Embodiments JJJ to OOO, further comprising a cleaning composition for periodically cleaning the polymeric tray.

Embodiment QQQ

The kit of Embodiment PPP, wherein the cleaning composition comprises a cleaning and disinfecting liquid.

Embodiment RRR

The kit of Embodiments PPP and QQQ, wherein the cleaning composition comprises a solid tablet dissolvable in water.

Embodiment SSS

The kit of any of Embodiments JJJ to RRR, wherein the refractive index of the aqueous liquid is greater than 1.33.

Embodiment TTT

The kit of any of Embodiments JJJ to SSS, wherein the viscosity modifier is a water soluble polymer chosen from polyacrylic acid, polyethylene glycol, ethylene oxide/propylene oxide copolymers, and combinations thereof, and wherein the water soluble polymer is present in the biocompatible aqueous liquid at about 0.5 parts by weight to about 60 parts by weight.

Embodiment UUU

The kit of any of Embodiments JJJ to TTT, wherein the silica compound comprises fumed silica.

Embodiment VVV

The kit of any of Embodiments JJJ to UUU, wherein the aqueous liquid has a pH of about 7.1 to about 7.35.

Embodiment WWW

The kit of any of Embodiments JJJ to VVV, wherein the aqueous liquid has a viscosity of about 0.001 Pa*s at shear rate 1/s to about 10 Pa*s at shear rate 1/s, at 20° C.

Embodiment XXX

The kit of any of Embodiments JJJ to WWW, wherein the calcium compound comprises calcium phosphate.

Embodiment YYY

The kit of any of Embodiments JJJ to XXX, wherein the polymeric shell and the aqueous liquid transmit at least 60% of incident light with a wavelength of about 400-750 nm.

Embodiment ZZZ

The kit of any of Embodiments JJJ to YYY, wherein the aqueous liquid is substantially transparent to visible light with a wavelength of 400-750 nm.

Embodiment AAAA

The kit of any of Embodiments JJJ to ZZZ, wherein the aqueous liquid comprises not greater than 4 wt % of a surfactant of formula I, based on the total weight of the composition:

$$HOCH_2-(CHOH)_n-CH_2NR^1R^2 \qquad (I)$$ 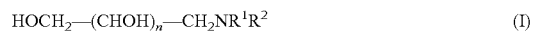

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group;

and n is an integer from about 2 to about 5.

Embodiment BBBB

The kit of any of Embodiments JJJ to AAAA, wherein the aqueous liquid comprises:
  about 0.1 parts by weight to about 60 parts by weight of a water soluble polymer;
  about 40 parts by weight to about 95 parts by weight of a buffering agent comprising a phosphate compound;
  up to about 1 part by weight of a tooth re-mineralizing agent comprising a calcium compound;
  about 0.1 part by weight to about 10 parts by weight of a flavoring agent; and water.

Embodiment CCCC

The kit of any of Embodiments JJJ to BBBB, wherein the polymeric shell is a polymeric material chosen from polyurethane, polyester, polyethylene terephthalate, polyethylene terephthalate glycol, poly cyclohexylenedimethylene terephthalate glycol, poly(meth)acrylates, and mixtures and combinations thereof.

Embodiment DDDD

The kit of any one of claims JJJ to CCCC, wherein at least one cavity in the polymeric shell of the dental appliance is configured to adjust a tooth from a maloccluded position to a desired position.

Various embodiments of the invention have been described. These and other embodiments are within the scope of the following claims.

We claim:
1. A system, comprising:
  a dental appliance comprising a polymeric shell with a plurality of cavities for receiving one or more teeth; and a biocompatible cosmetic aqueous liquid in the cavities of the polymeric shell of the dental appliance, the aqueous liquid comprising:
about 0.1 parts by weight to about 60 parts by weight of a viscosity modifier chosen from polysaccharides, water compatible polymers, silica compounds, and mixtures and combinations thereof;
about 40 parts by weight to about 95 parts by weight of a buffering agent chosen from phosphate, carbonate, citrate, and mixtures and combinations thereof,
up to about 1 part by weight of a tooth re-mineralizing agent, and
at least about 29 parts by weight of water,
wherein the aqueous liquid is a gel substantially free of tooth whitening agents and fluoride, and wherein the aqueous liquid has a refractive index of greater than 1.3 at room temperature.

2. The system of claim 1, wherein the polymeric shell is a polymeric material chosen from polyurethane, polyester, polyethylene terephthalate, polyethylene terephthalate glycol, poly cyclohexylenedimethylene terephthalate glycol, poly(meth)acrylates and mixtures and combinations thereof.

3. The system of claim 1, wherein the refractive index of the aqueous liquid is greater than 1.33.

4. The system of claim 1, wherein the refractive index of the aqueous liquid is greater than 1.34.

5. The system of claim 1, wherein the aqueous liquid has a pH of about 6.0 to about 8.0.

6. The system of claim 1, wherein the aqueous liquid has a pH of about 7.1 to about 7.35.

7. The system of claim 1, wherein the viscosity modifier is a polysaccharide chosen from ethyl cellulose, methyl cellulose, carboxymethyl cellulose, hydroxyethyl cellulose, hydroxypropyl cellulose, xanthan gum, agarose, carrageenan, and mixtures and combinations thereof.

8. The system of claim 7, wherein the polysaccharide is hydroxyethyl cellulose.

9. The system of claim 7, wherein the polysaccharide is ethyl cellulose.

10. The system of claim 1, wherein the viscosity modifier is a water compatible polymer that comprises a water-soluble polymer.

11. The system of claim 10, wherein the viscosity modifier is a water soluble polymer chosen from polyacrylic acid and salts thereof, polyethylene glycol, ethylene oxide/propylene oxide copolymers, and mixtures and combinations thereof.

12. The system of claim 1, wherein the viscosity modifier is a silica compound comprising a fumed silica.

13. The system of claim 1, wherein the aqueous liquid comprises not greater than 3 wt % of a silica-containing viscosity modifier.

14. The system of claim 1, wherein the buffering agent comprises a phosphate compound.

15. The system of claim 14, wherein the phosphate compound is $Na_2HPO_4$.

16. The system of claim 14, wherein the buffering agent further comprises a water soluble polymer.

17. The system of claim 1, wherein the tooth re-mineralizing agent comprises a calcium compound.

18. The system of claim 17, wherein the calcium compound comprises calcium phosphate.

19. The system of claim 1, wherein the aqueous liquid further comprises a flavoring agent.

20. The system of claim 19, wherein the flavoring agent is a polyol sugar alcohol.

21. The system of claim 20, wherein the polyol sugar alcohol is chosen from xylitol, erythritol, glycerol, sorbitol and mixtures and combinations thereof.

22. The system of claim 21, wherein the polyol sugar alcohol comprises xylitol.

23. The system of claim 1, wherein the aqueous liquid comprises a surfactant of Formula I:

$$HOCH_2-(CHOH)_n-CH_2NR^1R^2 \quad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group;
and n is an integer from about 2 to about 5.

24. The system of claim 23, wherein the surfactant of Formula I is present in the aqueous liquid at not greater than 4 wt %, based on the total weight of the aqueous liquid.

25. The system of claim 1, wherein the aqueous liquid further comprises sweeteners, humectants, mineral salts, buffering components, flavorants, preservative agents, or combinations thereof.

26. The system of claim 1, wherein the aqueous liquid further comprises aloe vera, folic acid, hyaluronic acid, ceramides, arginine, betaines or oxygenated glycerol triesters, vitamin E, vitamin B12, EDTA, cetyl pyridinium chloride, chlorhexidine, other antiseptics, or combinations thereof.

27. The system of claim 1, wherein the aqueous liquid is sprayable.

28. The system of claim 1, wherein the aqueous liquid prevents, inhibits, disrupts, or any combination thereof the formation or maintenance of a biofilm in an area contacted with the aqueous liquid.

29. The system of claim 1, wherein at least one cavity in the polymeric shell of the dental appliance is configured to adjust a tooth from a maloccluded position to a desired position.

30. A system, comprising:
a dental appliance comprising a polymeric shell with a plurality of cavities for receiving one or more teeth, wherein the polymeric shell is a polymeric material chosen from polyurethane, polyester, polyethylene terephthalate, polyethylene terephthalate glycol, poly cyclohexylenedimethylene terephthalate glycol, poly (meth)acrylates and mixtures and combinations thereof; and
a biocompatible cosmetic aqueous liquid in at least some of the cavities of the polymeric shell of the dental appliance, the aqueous liquid comprising:
about 0.1 parts by weight to about 60 parts by weight of a viscosity modifier chosen from polysaccharides, water compatible polymers, silica compounds, and mixtures and combinations thereof;
about 40 parts by weight to about 95 parts by weight of a buffering agent comprising a phosphate compound;
up to about 1 part by weight of a tooth re-mineralizing agent comprising a calcium compound; and
at least about 29 parts by weight of water;
wherein the aqueous liquid is a gel substantially free of tooth whitening agents and fluoride, and wherein a refractive index of the aqueous liquid is greater than 1.3, and the gel has a viscosity of about 0.001 Pa*s at shear rate 1/s to about 10 Pa*s at shear rate 1/s, at 20° C.

31. The system of claim 30, wherein the refractive index of the aqueous liquid is greater than 1.33.

32. The system of claim 30, wherein the refractive index of the aqueous liquid is greater than 1.34.

33. The system of claim 30, wherein the viscosity modifier is a water compatible polymer, wherein the water compatible polymer is a water soluble polymer chosen from polyacrylic acid, polyethylene glycol, ethylene oxide/propylene oxide copolymers, and combinations thereof, and wherein the water soluble polymer is present in the aqueous liquid at about 0.5 parts by weight to about 60 parts by weight.

34. The system of claim 30, wherein the silica compound comprises not greater than 3 wt % of a viscosity modifier comprising a fumed silica.

35. The system of claim 30, wherein the aqueous liquid has a pH of about 6.0 to about 8.0.

36. The system of claim 30, wherein the aqueous liquid has a pH of about 7.1 to about 7.35.

37. The system of claim 30, wherein the aqueous liquid further comprises about 0.1 part by weight to about 10 parts by weight of a flavoring agent comprising a polyol sugar alcohol.

38. The system of claim 37, wherein the polyol sugar alcohol comprises xylitol.

39. The system of claim 30, wherein the calcium compound comprises calcium phosphate.

40. The system of claim 30, wherein the polymeric shell and the aqueous liquid transmit at least 60% of incident light with a wavelength of about 400-750 nm.

41. The system of claim 30, wherein the aqueous liquid is substantially transparent to visible light with a wavelength of 400-750 nm.

42. The system of claim 30, wherein the aqueous liquid comprises not greater than 4 wt % of a surfactant of formula I, based on the total weight of the aqueous liquid: HOCH2-(CHOH)n-CH2N'R$^2$ (I) wherein R$^1$ and R$^2$ are independently selected from the group consisting of a hydrogen atom, an alkyl group, C(O)R$^3$, and SO2R$^4$; with R$^3$ and R$^4$ being independently selected from the group consisting of an alkyl group, an aryl group, and an aralkyl group; and n is an integer from about 2 to about 5.

43. The system of claim 30, wherein the aqueous liquid is sprayable.

44. The system of claim 30, wherein the aqueous liquid prevents, inhibits, disrupts, or any combination thereof the formation or maintenance of a biofilm in an area contacted with the aqueous liquid.

45. The system of claim 30, wherein at least one cavity in the polymeric shell of the dental appliance is configured to adjust a tooth from a maloccluded position to a desired position.

46. A kit, comprising:
a dental appliance comprising a polymeric shell with a plurality of cavities for receiving one or more teeth; and
a biocompatible cosmetic aqueous liquid comprising:
about 0.1 parts by weight to about 60 parts by weight of a viscosity modifier chosen from polysaccharides, water compatible polymers, silica compounds, and mixtures and combinations thereof;
about 40 parts by weight to about 95 parts by weight of a buffering agent chosen from phosphate, carbonate, citrate, and mixtures and combinations thereof,
up to about 1 part by weight of a tooth re-mineralizing agent, and
at least about 29 parts by weight of water,
wherein the aqueous liquid is a gel substantially free of tooth whitening agents and fluoride, and wherein the aqueous liquid has a refractive index of greater than 1.3 at room temperature.

47. The kit of claim 46, further comprising an applicator for applying the aqueous liquid to the dental appliance.

48. The kit of claim 46, further comprising instructions for applying the aqueous liquid to the dental appliance.

49. The kit of claim 46, further comprising a re-closable tray for retaining the polymeric shell.

50. The kit of claim 46, further comprising a dispenser to dispense the aqueous liquid into the dental appliance.

51. The kit of claim 50, wherein the dispenser is automated.

52. The kit of claim 46, further comprising a cleaning composition for periodically cleaning the polymeric tray.

53. The kit of claim 52, wherein the cleaning composition comprises a cleaning and disinfecting liquid.

54. The kit of claim 52, wherein the cleaning composition comprises a solid tablet dissolvable in water.

55. The kit of claim 46, wherein the refractive index of the aqueous liquid is greater than 1.33.

56. The kit of claim 46, wherein the viscosity modifier is a water soluble polymer chosen from polyacrylic acid, polyethylene glycol, ethylene oxide/propylene oxide copolymers, and combinations thereof, and wherein the water soluble polymer is present in the biocompatible aqueous liquid at about 0.5 parts by weight to about 60 parts by weight.

57. The kit of claim 46, wherein the silica compound comprises fumed silica.

58. The kit of claim 46, wherein the aqueous liquid has a pH of about 7.1 to about 7.35.

59. The kit of claim 46, wherein the aqueous liquid has a viscosity of about 0.001 Pa*s at shear rate 1/s to about 10 Pa*s at shear rate 1/s, at 20° C.

60. The kit of claim 46, wherein the re-mineralizing agent comprises calcium phosphate.

61. The kit of claim 46, wherein the polymeric shell and the aqueous liquid transmit at least 60% of incident light with a wavelength of about 400-750 nm.

62. The kit of claim 46, wherein the aqueous liquid is substantially transparent to visible light with a wavelength of 400-750 nm.

63. The kit of claim 46, wherein the aqueous liquid comprises not greater than 4 wt % of a surfactant of formula I, based on the total weight of the aqueous liquid: HOCH2-(CHOH)n-CH2NR'R$^2$ (I) wherein R$^1$ and R$^2$ are independently selected from the group consisting of a hydrogen atom, an alkyl group, C(O)R$^3$, and SO2R$^4$; with R$^3$ and R$^4$ being independently selected from the group consisting of an alkyl group, an aryl group, and an aralkyl group; and n is an integer from about 2 to about 5.

64. The kit of claim 46, wherein the polymeric shell is a polymeric material chosen from polyurethane, polyester, polyethylene terephthalate, polyethylene terephthalate glycol, poly cyclohexylenedimethylene terephthalate glycol, poly(meth)acrylates, and mixtures and combinations thereof.

65. The kit of claim 46, wherein at least one cavity in the polymeric shell of the dental appliance is configured to adjust a tooth from a maloccluded position to a desired position.

* * * * *

UNITED STATES PATENT AND TRADEMARK OFFICE
CERTIFICATE OF CORRECTION

| | | |
|---|---|---|
| PATENT NO. | : 11,642,199 B2 | Page 1 of 1 |
| APPLICATION NO. | : 16/140376 | |
| DATED | : May 9, 2023 | |
| INVENTOR(S) | : David Keith Cinader | |

It is certified that error appears in the above-identified patent and that said Letters Patent is hereby corrected as shown below:

In the Claims

<u>Column 31</u>
Line 34-35, In Claim 42, delete "HOCH2-(CHOH)n-CH2N'R2" and insert -- $HOCH_2\text{-}(CHOH)_n\text{-}CH_2NR^1R^2$ --, therefor.

Line 37, In Claim 42, delete "SO2R4" and insert -- $SO_2R^4$ --, therefor.

<u>Column 32</u>
Line 16 (approx.), In Claim 52, delete "polymeric tray" and insert -- polymeric shell --, therefor.

Line 34-35, In Claim 63, delete "HOCH2-(CHOH)n-CH2NR'R2" and insert -- $HOCH_2\text{-}(CHOH)_n\text{-}CH_2NR^1R^2$ --, therefor.

Line 37, In Claim 63, delete "SO2R4" and insert -- $SO_2R^4$ --, therefor.

Signed and Sealed this
Twenty-fourth Day of October, 2023

*Katherine Kelly Vidal*

Katherine Kelly Vidal
*Director of the United States Patent and Trademark Office*